(12) United States Patent
Knight et al.

(10) Patent No.: US 8,679,761 B2
(45) Date of Patent: Mar. 25, 2014

(54) METHOD FOR DETECTION OF INFLAMMATION IN THE URINARY TRACT OR URETHRA

(75) Inventors: Jan Knight, Plymouth (GB); Robert Knight, Plymouth (GB)

(73) Assignee: Knight Scientific Limited, Plymouth, Devon (GB)

( * ) Notice: Subject to any disclaimer, the term of this patent is extended or adjusted under 35 U.S.C. 154(b) by 0 days.

(21) Appl. No.: 13/634,495

(22) PCT Filed: Mar. 15, 2011

(86) PCT No.: PCT/GB2011/050512
§ 371 (c)(1),
(2), (4) Date: Oct. 22, 2012

(87) PCT Pub. No.: WO2011/114146
PCT Pub. Date: Sep. 22, 2011

(65) Prior Publication Data
US 2013/0143252 A1      Jun. 6, 2013

(30) Foreign Application Priority Data

Mar. 15, 2010 (GB) .................................. 1004235.6

(51) Int. Cl.
*C12Q 1/68* (2006.01)
(52) U.S. Cl.
USPC ...................................................... 435/6.15

(58) Field of Classification Search
USPC ........................................................ 435/6.15
See application file for complete search history.

(56) References Cited

PUBLICATIONS

Meenan B J et al., "Development of a sensitive whole blood chemiluminescence method for assessing the bioactivity of calcium phosphate powders," Biomaterials, Elsevier Science Publishers BV., Barking, GB, vol. 23, No. 12, pp. 2431-2445 (2002).

*Primary Examiner* — Maryam Monshipouri
(74) *Attorney, Agent, or Firm* — Bozicevic, Field & Francis LLP; Bret E. Field (57) ABSTRACT

A method for detecting inflammation in the urinary tract or urethra of a patient, especially urethritis, comprises a) contacting leucocytes obtained from a urine sample provided by the patient with a luminescence reagent which emits light on reaction with an oxidant; b) adding an activator to the mixture of leucocytes and luminescence reagent; c) continuously monitoring and/or measuring light emitted by the luminescence reagent over a predetermined time period commencing before and ending after the addition of the activator. The light emission is indicative of the presence or absence of inflammation in the urinary tract or urethra of the patient. The urine sample is preferably a sample of first pass urine. The method makes possible a diagnosis especially of urethritis and, in particular, urethral infections selected from *Chlamydia trachomatis* and *Neisseria gonorrhoeae*, which can be carried out quickly without invasive procedures. A diagnostic kit for carrying out the method, comprising a luminescence reagent which emits light on reaction with an oxidant, an activator and a library of standard signature light emission curves is also disclosed.

12 Claims, 8 Drawing Sheets

METHOD FOR DETECTION OF INFLAMMATION IN THE URINARY TRACT OR URETHRA

The present invention relates to a method for detecting inflammation in the urinary tract or urethra of a patient, especially the detection of urethritis. The invention, further, relates to methods of diagnosing urethral infections such as *Chlamydia trachomatis, Neisseria gonorrhoeae* or non-specific urethritis in a patient. In addition, the invention relates to a diagnostic kit useful for carrying out such a diagnosis.

BACKGROUND OF THE INVENTION

Inflammation in the urinary tract or urethra of a patient which is usually, though not necessarily, due to bacterial infection is a condition requiring diagnostic accuracy by healthcare professionals. This is particularly critical for the diagnosis of sexually transmitted infections.

Sexually transmitted infections (STIs) are a major global cause of acute illness, infertility, long-term disability and death. Over the past decade, there has been a substantial increase in diagnoses of most sexually transmitted diseases in the UK. Overall, the increase between 1998 and 2008 has been approximately 60% with uncomplicated *Chlamydia* showing an increase of approximately 150% over the same period. The UK Government has responded by investing money in Genito-Urinary Medicine clinics and in public education. Increasing public awareness of the problems leads to an increase in the numbers of people wanting to be tested. The situation is very similar in the USA where approximately 19 million new STIs have occurred each year with almost half of them among young people of 15 to 24 years of age. Many infections can be treated and cured relatively easily and inexpensively if diagnosed sufficiently early. If, however, an infection is left untreated, many serious complications can occur. STIs can be passed from mother to baby before, during, or immediately after, birth. Such an infection has the potential to disable or kill the baby. Individuals, not aware that they are infected, innocently pass the infection on to their sex partners. Periodic, or even frequent, testing or screening of individuals is, for obvious reasons, recommended for individuals who change their sex partners.

Diagnosis of urethritis is conventionally carried out by light microscopical identification of Gram-stained urethral smears or by testing for leucocyte esterase (LE) in urine using dipsticks. Typically, an urethral smear is obtained using a swab or microbiological loop. Inflammation of the urethra is associated with an accumulation of polymorphonuclear leucocytes (also known as neutrophils) on its inner surface usually in response to the presence of bacteria associated with STIs. Microscopy has the merit of allowing a diagnosis to be made relatively quickly, for instance in less than 30 minutes, and therefore enables treatment of the patient at the first visit to a clinic, rather than having to wait for the results of laboratory tests for the causative agents to be made available. Although microscopical testing can be quick, this relies on the production of a urethral smear, an uncomfortable, invasive procedure which may deter men, in particular, from seeking diagnosis.

One alternative to urethral smears is a test developed over 20 years ago which determines the number of leucocytes in urine by measuring the concentration of the enzyme leucocyte esterase (LE) using dipstick tests. The LE test is attractive as a screening tool since it is inexpensive, non-invasive and easy to use in an outpatient setting. However, while it is capable of identifying a large proportion of *Chlamydia* urethral infections, it misses many other infections.

WO 98/11259 describes the testing of genitourinary body fluid samples using a nucleic acid amplification technique (NAAT) to detect a plurality of sexually transmitted disease pathogens including *Chlamydia trachomatis, Neisseria gonorrhoeae, Mycoplasma genitalium* and *Ureaplasma urealyticum*. Examples of genitourinary body fluid samples that are suitable for use in the test procedure according to WO 98/11259 include first pass urine. It is noted here that first pass urine is usually the easiest sample to obtain from a patient.

It is, however, thought that testing techniques based on nucleic acid amplification are not able to identify infections in all tested patients who are actually infected. In cases where an infected male is wrongly tested negative, a female partner may be at increased risk of *Chlamydia trachomatis* infection.

An aim of the present invention is to solve the problems of the prior art procedures by providing a quick, point-of-care testing procedure which is more sensitive and more selective than prior art procedures which can be carried out on a urine sample provided by a patient.

SUMMARY OF THE INVENTION

The present invention provides a method for detecting inflammation in the urinary tract or urethra of a patient, which method comprises
a) contacting leucocytes obtained from a urine sample provided by the patient with a luminescence reagent which emits light on reaction with an oxidant;
b) adding an activator to the mixture of leucocytes and luminescence reagent;
c) continuously monitoring and/or measuring light emitted by the luminescence reagent over a predetermined time period commencing before and ending after the addition of the activator, this light emission being indicative of the presence or absence of inflammation in the urinary tract or urethra of the patient.

In the case where a urinary tract infection is suspected, the urine sample used for the collection of leucocytes to be tested will preferably be a sample of midstream urine.

According to a preferred embodiment, the invention provides a method for detecting urethritis in a patient comprising:
a) contacting urethral leucocytes obtained from a urine sample provided by the patient with a luminescence reagent which emits light on reaction with an oxidant;
b) adding an activator to the mixture of leucocytes and luminescence reagent;
c) continuously monitoring and/or measuring light emitted by the luminescence reagent over a predetermined time period commencing before and ending after the addition of the activator, this light emission being indicative of the presence of or the absence of urethritis in the patient. Preferably, the urine sample used in the method for detecting urethritis is first pass urine. The luminescence reagent used is preferably the photoprotein derived from *Pholas dactylus* (the photoprotein is available commercially as "Pholasin", a registered trademark of Knight Scientific Limited).

According to a preferred embodiment, the invention provides a method of diagnosing an urethral infection selected from *Chlamydia trachomatis* and *Neisseria gonorrhoeae* in a patient comprising:
a) contacting urethral leucocytes obtained from a sample of first pass urine provided by the patient with a luminescence reagent which emits light on reaction with an oxidant;

b) adding an activator to the mixture of leucocytes and luminescence reagent;
c) continuously measuring light emitted by the luminescence reagent over a predetermined time period commencing before and ending after the addition of the activator, and producing therefrom a light emission curve;
d) comparing the light emission curve with standard signature light emission curves obtained for leucocytes known to be infected by *Chlamydia trachomatis* or *Neisseria gonorrhoeae;*
e) diagnosing the presence or absence of infection from the result of the comparison in step d).

Preferably, the luminescence reagent used in the diagnostic methods of the invention is the photoprotein derived from *Pholas dactylus* ("Pholasin", a registered trademark of Knight Scientific Limited). The activator, which is added to the mixture of the leucocytes derived from the patient and the luminescence reagent, may be any composition which has the effect of activating the luminescence reagent to emit light. Preferably, the activator is selected from N-formyl-methionyl-leucyl-phenylalanine and Phorbol-12-myristate-13-acetate. The present invention, in a further aspect, provides a diagnostic kit for use in carrying out the diagnostic method of the invention which kit comprises:
a) a luminescence reagent which emits light on reaction with an oxidant;
b) an activator;
c) a library of standard signature light emission curves obtained for leucocytes known to be infected by *Chlamydia trachomatis* or by *Neisseria gonorrhoeae.*

DETAILED DESCRIPTION OF THE INVENTION

The method for detecting urethritis in a patient comprises, according to the present invention:
a) contacting urethral leucocytes obtained from a urine sample provided by the patient with a luminescence reagent which emits light on reaction with an oxidant;
b) adding an activator to the mixture of leucocytes and luminescence reagent;
c) continuously monitoring and/or measuring light emitted by the luminescence reagent over a predetermined time period commencing before and ending after the addition of the activator, this light emission being indicative of the presence or absence of urethritis in the patient.

The method of the invention is carried out using urethral leucocytes obtained from a urine sample provided by the patient. Preferably, the sample will be of first pass urine, also known as first catch urine, since this portion of urine voided by a patient which is not diluted by midstream urine will contain the greatest concentration of leucocytes from the urethra. Various urine collection devices have been proposed for the collection of a sample of urine for medical testing. Some devices are constructed so as to collect preferentially one part of the urine voided by a patient with the unwanted part(s) of the urine being discarded. A device which is specifically designed to collect a sample of the first pass portion of urine voided by a donor which portion is isolated from the midstream portion of the urine comprises a first part comprising an opening at its upper end adapted to receive urine voided by the donor, a urine collection body downstream of the upper end and a closeable exit located downstream of the urine collection body and at the lower end of the first part, the exit providing a circular orifice, and a second part located downstream of the exit of the first part and comprising a tube at its upper end which is in communication with the exit of the first part, the second part having a closed lower end, wherein the circular orifice provided by the exit of the first part defines an inlet into the second part and has a diameter which is smaller than the diameter of the tube at the upper end of the second part, and wherein the second part contains a moveable closure member for blocking the inlet into the second part which moveable closure member is capable of floating in urine and is adapted such that, in use, it blocks the inlet into the second part on the filling of the second part with urine so as to cause further voided urine to be collected in the urine collection body of the first part. Preferably, the second part of the device is capable of being detached from the first part of the device such that the second part of the device, which after use will contain first pass urine, can be separated from the remaining parts of the device and, subsequently, capped or closed by a cap or a lid so that the sample of first pass urine collected in the second part of the device can be stored or moved without suffering contamination or spillage. Such a device is disclosed in our co-pending International Application PCT/GB2009/051561.

The sample of urine collected from the patient for testing according to the method of the present invention, which preferably is a sample of first pass urine which is not diluted by midstream urine as stated above, will preferably be subjected to treatment to concentrate the leucocytes present in the urine sample. Preferably, the leucocytes will be separated from the liquid portion of the urine sample and, typically, such separation will be achieved by subjecting the sample to centrifugation or by passing the collected urine sample or part thereof through a filter such that the leucocytes are retained on the filter and the liquid portion of the urine sample passes through the filter. The leucocytes are, of course, very small compared to the filter. Leucocytes typically have diameters of about 15 μm and, therefore, care has to be exercised in their collection on a filter material and, subsequently, if necessary, removing the collected leucocytes, after collection, from the filter material to avoid damage to the leucocytes to be used in the method of the invention. WO 94/23296 discloses a method of separating particles, such as leucocytes, from a filter to minimise damage to the particles and such a method is useful for obtaining leucocytes for testing in the present invention. The filter material that may be used to separate the urethral leucocytes from the urine sample will typically be one capable of selectively retaining the leucocytes by adsorption when the urine containing the leucocytes is passed or drawn through it. It may be comprised of one or more membranes of a suitable material or may have a fibrous or particulate composition. Preferably, the filter material will have a critical wetting surface tension greater than 53 dynes/cm so that the leucocytes are held to the filter material by adsorption. Filter materials useful for separating the urethral leucocytes from a urine sample containing them are known in the art.

If the urine sample containing the urethral leucocytes is passed through a filter material, the filter material is preferably, initially, wetted to prepare the filter material for the filtration step, although satisfactory results can be obtained even if the filter is not wetted. Typically, a physiological buffer is used to wet the filter material. This buffer may be heated to an elevated temperature prior to use, i.e. up to 40° C., although typically it will be at a temperature of about 37° C. Since leucocytes are more retentive at higher temperatures, such a rise in temperature will improve leucocyte collection. Furthermore, an increased temperature will reduce the viscosity of the urine sample and, since filtration can be difficult at low Reynolds number with high pressure drops across the filter, the reduction in viscosity during the filtration step will increase the rate and efficiency of the filtration. Preferably, the filter material is wetted with phosphate buffered saline (PBS), made up with: 0.8 g NaCl; 0.02 g KCl; 0.115 g $Na_2HPO_4.2H_2O$; 0.02 g $KH_2PO_4$ per 100 ml solution.

Following any prior wetting step, the urine sample containing the leucocytes to be removed by adsorption on a filter material is delivered on to the filter material. Various techniques may be employed to deliver the urine sample on to the filter material. Examples include the use of a syringe or pipette, or delivery from a tube or any other vessel into which the urine sample has been temporarily stored prior to transfer to the filter.

The urine may be drawn through the filter, for instance by way of a vacuum or pushed through the filter by direct pressure. Various devices can be made to hold one or a number of samples of urine and the filtration step can be carried out manually or automatically, even controlled by a computer. As the fluid passes through the filter material, the leucocytes become adsorbed on to the filter material and, thereby, become retained thereon. The non-adsorbed components of the urine sample pass through the filter material and may be collected in a container. The container may be an absorbent pad as described in EP-A-0489602 although, preferably, is a closable vessel to enable safe disposal without contamination or leakage of the contents.

Following the filtration step, which is completed in a few seconds, the filter material together with the adsorbed leucocytes is washed preferably with a physiological buffer, such as a phosphate buffered saline containing no calcium or magnesium ions but to which albumin or gelatine at a concentration of 0.1% may have been added to good effect. This washing buffer may be preheated to an elevated temperature to aid the removal of the leucocytes from the filter material. In a typical embodiment, the washing buffer will be preheated to a temperature of about 37° C. The volume of washing buffer used in the washing step will, in general, be from 1 to 6 times, preferably about 4 times, the volume of the fluid subjected to filtration. Essential to the procedure to ensure quiescence of leucocytes and to prevent clotting is the absence of calcium and magnesium salts from the washing buffer.

The filter material having the leucocytes adsorbed thereon is then preferably placed in a liquid medium which is typically aqueous and preferably sterile and is subjected to agitation of sufficient magnitude to create turbulence in the tube, or other vessel, setting the liquid and filter into turbulent or random motion and thus creating shear forces, in many directions, on the filter whilst leaving the particles, not affected by the turbulent flow, in suspension in the liquid and then separating the liquid with liberated particles, from the filter. The liquid, preferably aqueous, will usually be contained in a receptacle and the filter material having adsorbed particles will be transferred from the filter apparatus to the receptacle and, thus, brought into contact with the liquid medium in which particle removal from the filter material will be effected. The aqueous medium is, typically, a physiological buffer such as phosphate buffered saline. The temperature of this medium when it contacts the filter material may generally be from 0° C. to about 40° C. However, we have found that the removal of the leucocytes from the filter material is facilitated by locating the filter material in an aqueous medium having a low temperature. Preferably, then, the temperature of the aqueous medium, when it contacts the filter material and adsorbed particles, will be less than 10° C., preferably from 1° to 8° C., especially about 4° C. Reducing the temperature has the effect of increasing the viscosity of the liquid medium and thus reducing the Reynolds number further.

According to the above-described procedure, the leucocytes are released into the aqueous medium which can be decanted from, or otherwise separated from, the filter material.

If a centrifugation technique is used to separate the leucocytes from the urine sample, we have found that centrifugation at 3000 rpm for about 10 minutes followed by re-suspension of the cells obtained and then further centrifugation at 5000 rpm for a few minutes is sufficient. The cells obtained are then, preferably, washed prior to re-suspension in blood dilution buffer for use in the light activation assay.

The leucocytes obtained from the urine sample are, according to the invention, contacted with a luminescence reagent which emits light on reaction with an oxidant. Such luminescence reagents, generally, are well-known in the art and examples include lucigenin, luminol (3-aminophthalhydrazide, 5-amino-2,3-dihydro-1,4-phthalazinedone), isoluminol (4-aminophthalhydrazide), MCLA (6-(methoxyphenyl)-2-methyl-3,7-dihydroimidazol[1,2-a]pyrazine-3(7H)-one hydrochloride and PHOLASIN™ which is the photoprotein derived from the marine bivalve mollusc *Pholas dactylus*. PHOLASIN™ is preferred for use in the present invention in view of its ultrasensitivity towards free radicals such as the superoxide anion and other reactive oxygen-containing species (ROS) as well as its ability to react with enzymes such as peroxidases. It is also possible to use a synthetic equivalent of the photoprotein derived from *Pholas dactylus*.

An activator is added to the mixture of leucocytes and luminescence reagent to stimulate the NADPH oxidase system of the leucocytes. Through this stimulation, free radicals and/or reactive oxygen species produced excite the luminescence reagent resulting in the emission of light by the reagent. Examples of activators that may be used in the method of the present invention include the receptor stimulant N-formyl-methionyl-leucyl-phenylalanine (fMLP) and the phorbol ester, Phorbol-12-myristate-13-acetate (PMA) which enters the cell and activates protein kinase C directly. Presentation of fMLP and PMA together enables the activation of the NADPH oxidase on the cell surface to be monitored simultaneously with the activation of the NADPH oxidase on the membrane of secondary granules. PMA activates the NADPH oxidase throughout the cell, but at a slower rate than fMLP and it also promotes degranulation. In addition, platelet activating factor (PAF) which binds to fMLP receptors and also enters the cell acts in a similar way to using a combination of fMLP and PMA. Other mediators, such as anti-Fc receptor antibodies, activated complement and lipopolysaccharides (LPS) may also be used in concentrations that either prime the cell to respond to fMLP or at higher concentrations to actually stimulate the production of free radicals. These mediators, in addition to stimulating the production of free radicals, can also promote the release of enzymes from various granules within the leucocytes.

Light that is emitted by the luminescence reagent is monitored and/or measured over a predetermined time period which commences before the addition of the activator to the mixture of luminescence reagent and leucocytes and which ends after the addition of the activator. In the case of the luminescence reagent PHOLASIN™, a low level light, known as the resting glow, is emitted before the leucocytes are activated but, on the addition of the activator, light emission is greatly increased if the leucocytes are derived from a site of inflammation. Thus, over the predetermined time period during which light emission is monitored and/or measured, the effect of the addition of the activator to the leucocyte/luminescence reagent mixture is seen. The predetermined time period will be chosen depending on the concentration of leucocytes and/or luminescence reagent in the test solution but will typically be less than 30 minutes, preferably less than 20 and more preferably less than 15 minutes.

The emission of light by the luminescence reagent is preferably recorded with respect to time over the predetermined period of time. A plot of emitted light intensity against time produces a light emission curve which, for certain STIs, shows a characteristic shape.

Figure 1:
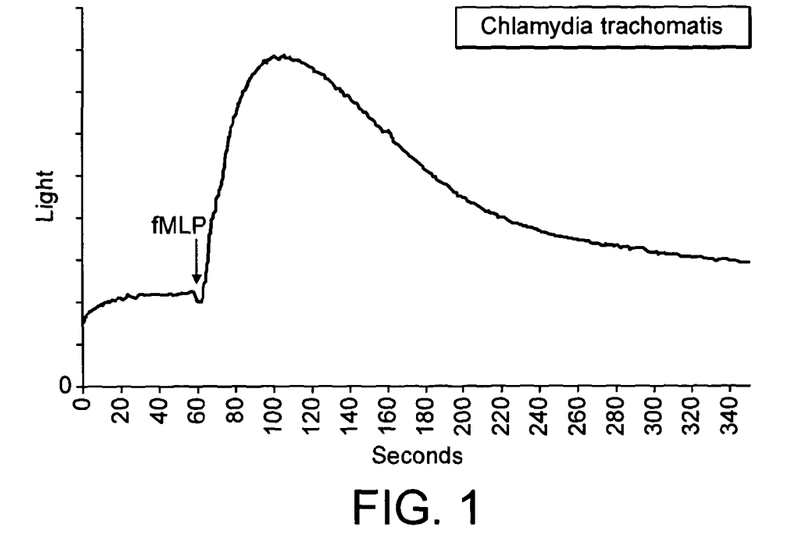
FIG. 1 provides a light emission curve produced using leucocyte samples from a patient, who, independently, was clinically diagnosed as *Chlamydia* positive (no other infection agents being present).
Figure 2:
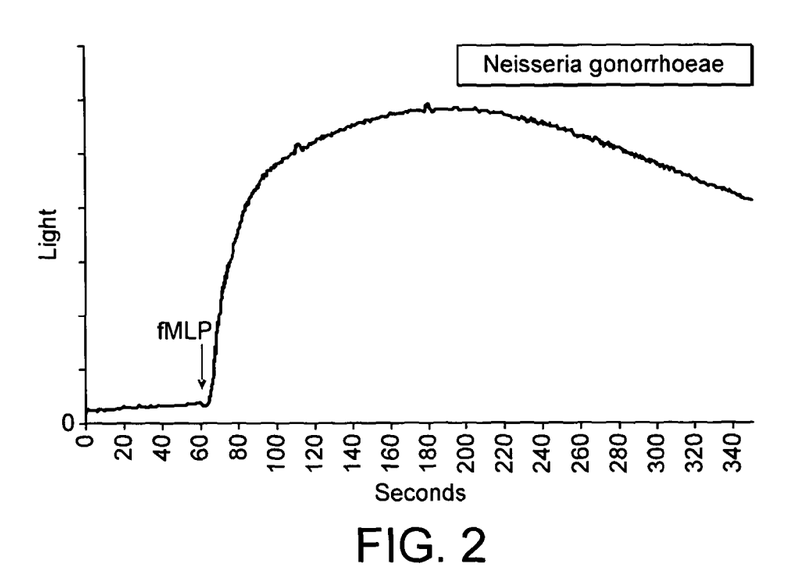
FIG. 2 provides a light emission curve produced using leucocyte samples from a patient, who, independently, was clinically diagnosed as *Neisseria gonorrhoeae* positive (no other infection agents being present).

Through our research we have found, surprisingly and unexpectedly, that light emission curves produced using leucocyte samples from patients, who, independently, are clinically diagnosed as *Chlamydia* positive (no other infection agents being present), have a characteristic shape which is shown in FIG. 1. This shape is characterised by a steep rise in light emission, immediately after the addition of the activator, to a peak followed by a significant decrease in light emission after the peak. Additionally, we have found that light emission curves produced from leucocyte samples from patients, who, independently, are clinically diagnosed by gram positive staining of cells from an urethral smear to be positive for *Neisseria gonorrhoeae* (with no other infection agents being present), have a shape which is different from the characteristic shape shown for the *Chlamydia* positive patients. The curve shape obtained for *N. gonorrhoeae* positive patients is shown in FIG. 2. This shape is characterised by an intense rounded increase in light emission which, after peaking, decreases very gradually. Our research also demonstrates that the magnitude of the light response corresponds to the degree of infection in the patient.

It is, according to the present invention, possible to produce a library of standard signature light emission curves against which a light emission curve obtained using a sample obtained from a patient may be compared. Using such a comparison against standard signature curves, it is possible to not only confirm that a patient is indeed infected but also to identify whether the STI pathogen involved is *Chlamydia trachomatis* or *Neisseria gonorrhoeae*.

Accordingly, it is possible to diagnose the bacterial STI pathogen in a patient's sample as being one of *Chlamydia trachomatis* or *Neisseria gonorrhoeae*, by comparing the light emission curve produced using the sample with the distinctive characteristic curve shapes for *Chlamydia trachomatis* and for *Neisseria gonorrhoeae*.

According to a preferred embodiment of the invention, there is provided a method of diagnosing an urethral infection selected from *Chlamydia trachomatis* and *Neisseria gonorrhoeae* in a patient comprising:

a) contacting urethral leucocytes obtained from a sample of first pass urine provided by the patient with a luminescence reagent which emits light on reaction with an oxidant;

b) adding an activator to the mixture of leucocytes and luminescence reagent;

c) continuously measuring light emitted by the luminescence reagent over a predetermined time period commencing before, and ending after, the addition of the activator and producing therefrom a light emission curve;

d) comparing the light emission curve obtained in step c) with standard signature light emission curves obtained for leucocytes known to be infected by *Chlamydia trachomatis* or by *Neisseria gonorrhoaea*; and e) diagnosing the presence or absence of infection from the result of the comparison in step d).

Preferably, the luminescence reagent used in the method of this preferred embodiment is the photoprotein derived from *Pholas dactylus* (PHOLASIN™). Preferably, the activator used in the method of this preferred embodiment is selected from N-formyl-methionyl-leucyl-phenylalanine (fMLP), platelet activating factor and Phorbol-12-myristate-13-acetate. The method is particularly useful for diagnosing the presence of infection in male patients.

Light emission curves produced according to the method described above may indicate an abnormal response even though such curves do not have the characteristic shapes associated with *Chlamydia* or with *Neisseria* infections as shown in FIG. 1 or FIG. 2. It is, thus, possible according to the present invention to diagnose non-specific urethritis in a patient since an abnormal light emission curve which has neither the characteristic *Chlamydia* or *Neisseria* shapes is indicative of the presence of one or more other infection agents, possibly also in combination with *Chlamydia* and/or *Neisseria*.

The present invention, further, provides a diagnostic kit for use in carrying out the diagnosis of urethral infections such as *Chlamydia trachomatis* and *Neisseria* gonorrhoaea, according to the methods described above. The diagnostic kit of the invention comprises:

a) a luminescence reagent which emits light on reaction with an oxidant;

b) an activator; and c) a library of standard signature light emission curves obtained for leucocytes known to be infected by *Chlamydia trachomatis* or by *Neisseria* gonorrhoaea.

Preferably, the luminescence reagent provided in the diagnostic kit is the photoprotein derived from *Pholas dactylus* (PHOLASIN™). Preferably, the activator provided in the diagnostic kit of the invention is selected from N-formyl-methionyl-leucyl-phenylalanine (fMLP), platelet activating factor and Phorbol-12-myristate-13-acetate.

The library of standard signature curves may be provided on any suitable format, for example, printed on a substrate such as paper, card or a fabric or provided in a computer-readable form, such as a disk or other storage device.

The diagnostic kit may also contain a disposable device for collecting a sample of first pass urine from a patient for use in providing urethral leucocytes for testing.

The shapes of the light emission curves obtained according to the present invention are dependent on the response of the leucocytes, in terms of the production of free radicals and/or other active substances, to activation by an activator. These responses are dependent on the physiological state of the leucocytes in the urine and are thus related to the physiological or medical state of the patients from whom the urine samples were obtained. While such subjective observations of the shapes of the curves are of great value in making diagnoses, a method of quantifying the curves would lead to a more objective determination of irregularities in the leucocytes in the urine and, hence, a more objective diagnosis.

The curves consist of a plot of the response of a luminometer in terms of Relative Light Units (RLU) in three parts. The first part records the light emission before the stimulation of the leucocytes by the activator and may be analysed separately, if at all. The major part of the curve consists of a rise followed by a fall. The whole of this part of the curve can be analysed as one unit or it can be divided into the rising part and the falling part and the two parts analysed separately.

Suitable software can be used to derive a cubic expression of the general form $y=ax^3+bx^2+cx+d$, where $y=$RLU and $x=$time elapsed in seconds. By comparing values of a, b, c and d, calculated from different curves, it is possible to make a quantitative, and therefore more objective, comparison of the responses obtained using urine samples from different patients.

The method of the present invention can be carried out using conventional apparatus capable of monitoring and/or measuring light emitted by a luminescence reagent in the presence of activated leucocytes. The method is suitable for being carried out in a hand-held luminometer which is highly portable, compact and simple to use. Such a device comprises a means for containing a mixture of the leucocyte sample to be analysed and the luminescence reagent, a means for introducing, into the mixture, an activator, a means for monitoring and/or measuring light emitted by the luminescence reagent over a period of time commencing before and ending after the introduction of the activator, a display for displaying the light emitted by the luminescence reagent; the device being capable of being gripped in one hand.

EXAMPLE 1

Figure 3:
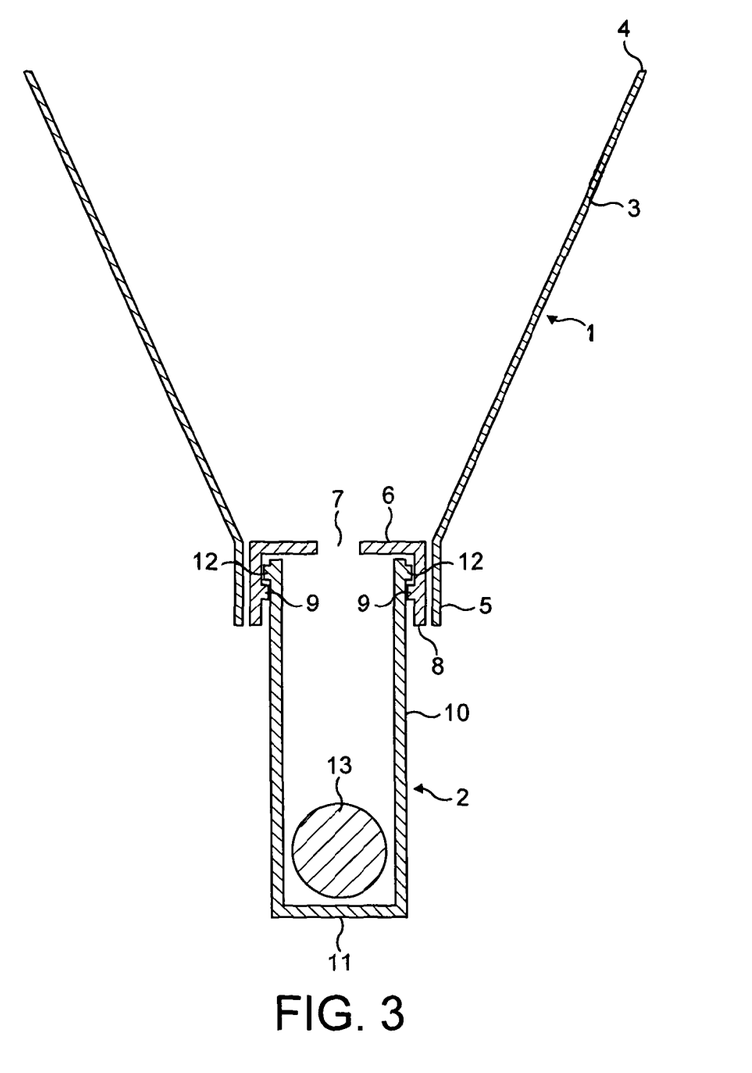
FIG. 3 provides an illustration of a device employed to collect urine samples, as reported in Example 1 below.

A. Samples of first pass urine were collected from 164 male patients. The first pass urine was collected using a device according to our co-pending International Application PCT/GB2009/051561 filed 18 Nov. 2009. This device, which is illustrated in FIG. 3, comprises a first part 1 and a second part 2. The first part 1 comprises a funnel 3 having a larger end 4 and a narrower end 5. The funnel may be of any suitable size or dimension. It may also be provided with a gulley to direct urine flow to the narrower end. The larger end 4 provides a receiving end for placing adjacent a donor to collect urine. Fitted within the narrower end 5 is an exit element 6 containing an orifice 7 defining an outlet into the second part 2. The exit element 6 has a side wall 8 which forms a seal with the internal surface of the narrower end of the funnel. The internal surface of side wall 8 is provided with a flange 9. The second part 2 of the device, which is located downstream of the exit element 6 of the first part, comprises a container 10 having a closed end 11. Prior to use of the device of the invention, a container having the desired capacity will be selected depending on the volume of the sample of first pass urine required. The container 10 comprises a tube at its end which is in communication with the exit element 6. The external surface of container 10 adjacent its upper end is provided with a screw thread 12 which engages with the flange 9 provided on the internal surface of the side wall 8 of the exit element 6. The container 10 contains a spherical bead 13 which is freely moveable within the container and which is buoyant in urine. The device may be held in a stable arrangement adjacent the donor, during use, by means of a support (not shown).

In use, the donor places the device of the invention in an appropriate position so that urine may be voided into the funnel 3. The voided urine flows into the funnel 3 and passes through orifice 7 of exit element 6 into the container 10. As the level of urine in container 10 rises, the buoyant spherical bead 13 floats at the surface of the urine in the container and so rises as the level of the urine rises in the container. When the level of first pass urine in the container reaches its maximum, the spherical bead 13 is pushed upwards against the orifice 7 so as to close the orifice to prevent further urine passing through into the container 10. Further urine voided by the donor is then collected in the body of the funnel.

When the donor has finished voiding urine, the urine collected in the body of the funnel may be discharged into a suitable waste outlet or transferred to another container, if it is to be analysed. Tipping of the funnel to remove the urine contained in the body of the funnel can be achieved without loss of the first pass urine in the container 10. The container, containing a sample of first pass urine, may then be detached from the first part of the device by unscrewing it from the flange 9 and then fitting with a suitable cap or lid to prevent contamination or spillage of the contents of the container.

B. After the first pass urine had been collected, 5 ml of each sample was submitted to a hospital microbiology laboratory for testing according to conventional laboratory procedures (smear tests and/or nucleic acid amplification in the case of *Chlamydia*, gram positive staining of urethral smears for other infection agents).

C. For the testing according to the present invention, leucocytes were collected from the urine samples by centrifugation. Typically, one 10 mL sample of urine was harvested for cell activation assays unless otherwise stated. Initially monovettes were centrifuged at 3000 rpm for 10 minutes and 9 mL of the supernatant removed. One mL of this supernatant was kept and stored at −80° C. Resulting pellets were re-suspended in the remaining urine (1 mL) and transferred to 1.7 mL microcentrifuge tubes which were centrifuged at 5000 rpm for 3 minutes. The urine supernatant was removed, and the pellets washed/re-suspended in 0.5 mL of fresh blood dilution buffer. This washing step was repeated once. After the second wash, supernatant was removed and the pellet re-suspended in 500 μL of blood dilution buffer and this suspension was used for cell activation tests.

D. 100 μL of cell suspension was mixed with 250 μL of Pholasin® (2.5 μg/ml) ("Pholasin" is a registered trade mark of Knight Scientific Limited), 100 μL Adjuvant-K™ ("Adjuvant-K" is a registered trade mark of Knight Scientific Limited) and 450 μL of cell activation reconstitution and assay buffer (from ABEL Cell Activation test kit obtained from Knight Scientific Limited) in 12 mm×75 mm round bottomed polypropylene cuvettes (Medfor Products). The assay mixture was incubated at 37° C. for 5 minutes. Background luminescence was then measured in a tube luminometer (BioOrbit 1251) at 1 second intervals for 1 minute after which time 100 μL of 10 μmol $L^{-1}$ fMLP (formyl-methionyl-leucyl-phenylalanine) or 100 μL PMA (Phorbol-12-myristate-13-acetate) 5 μg $mL^{-1}$ was automatically injected into the assay mixture, giving a total volume of 1 mL. Light output was measured for a further 5 minutes. In a few cases 100 μL of sample produced such a high signal that the luminometer was not able accurately to record it. On these occasions, a smaller sample size was used in the assay mixture (5 μL of sample, 545 μL assay buffer) and the result normalised to a 100 μL.

Results

Conventional Testing Procedure

Samples of the urine collected from each of the 164 patients were subjected to conventional clinical testing procedures in a hospital microbiology laboratory. The clinical testing identified 24 of the 164 patients (14.6%) as being *Chlamydia* positive and 17 (10.4%) were diagnosed (as a result of the clinical testing) with non-specific urethritis.

Present Invention

Figure 4A:
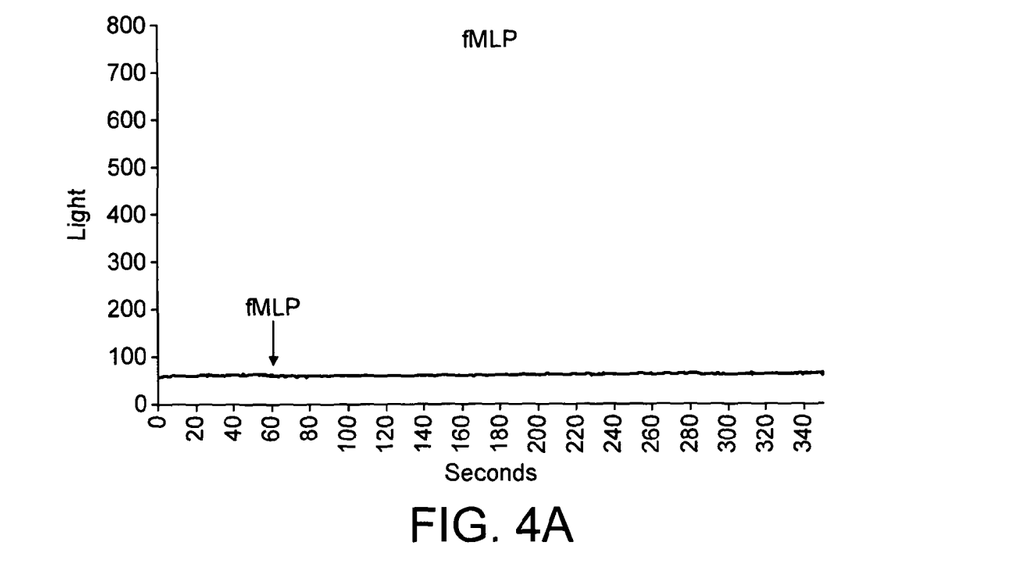
FIGS. 4A and 4B provide negative response curves following activation by fMLP or PMA, respectively.
Figure 4B:
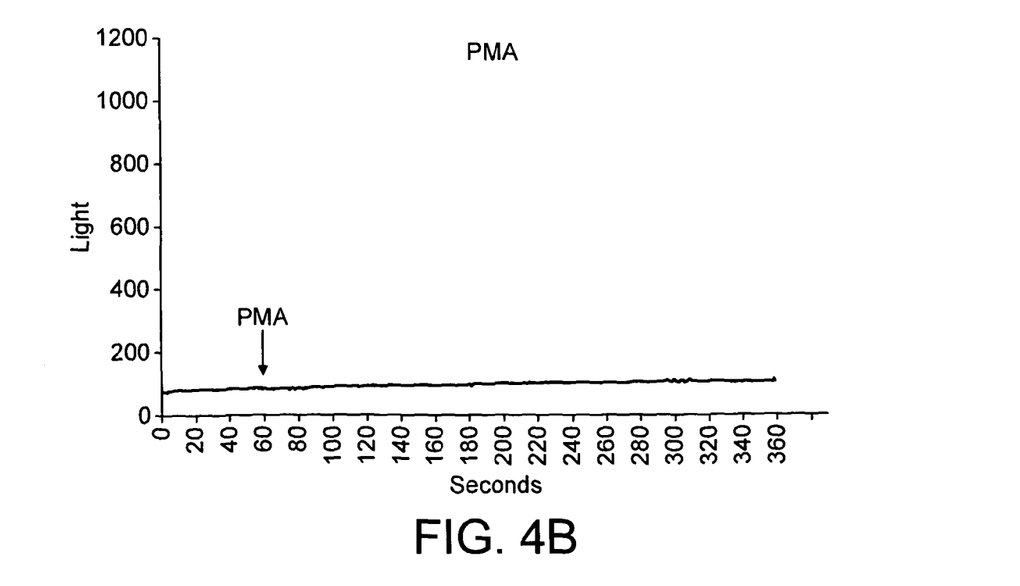

Light response curves were produced according to the present invention using the urine samples obtained from all 164 patients. The light response curves were produced using, as activator, either the stimulant fMLP or PMA, as described above. Light response curves showing no significant light output from the sample before or after the addition of the activator are indicative of a negative response. As such, a negative response does not indicate the presence of inflammation in the urethra or urinary tract, generally, in the patient. An example of a typical negative response obtained according to the test is shown in FIG. 4A (using fMLP) and 4B (same sample but using PMA). A light response curve showing a significant increase in the light signal after activation by the addition of either fMLP or PMA is indicative of a positive response indicating the presence of abnormal cell matter in the urine sample tested. An increase in the light signal prior to the addition of the activator may also be detected.

Figure 5A:
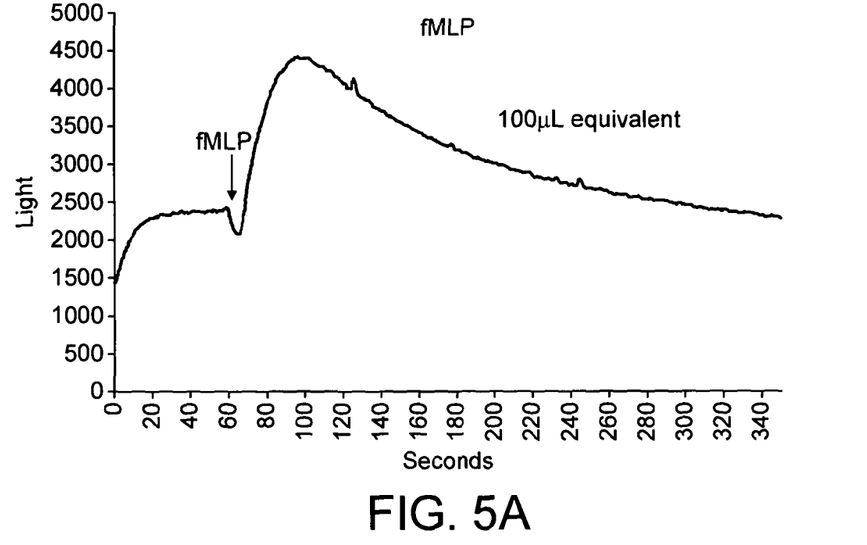
FIGS. 5A and 5B provide positive response curves following activation by fMLP or PMA, respectively.
Figure 5B:
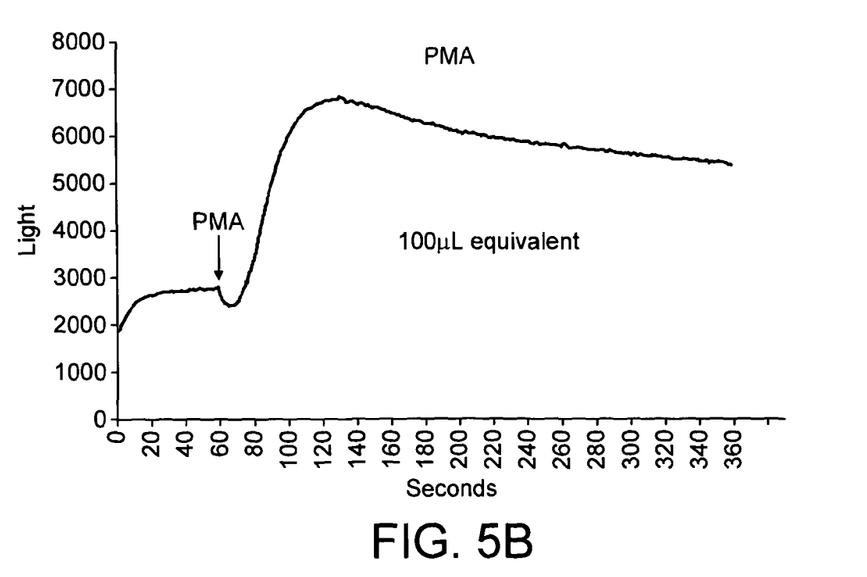

Twenty three of the light response curves produced were seen to have a common shape characterised by a slight increase in light output over the period from measurement commencement up to the time at which the activator (fMLP or PMA) was added to the sample and also, immediately after the addition of the activator to the sample, a steep rise in light output up to a peak value which peak is then immediately followed by a tailing off in light output. Examples of such light response curves are shown in FIG. 5A (using fMLP) and 5B (same sample but using PMA). It was found that these 23 common-shaped light response curves were produced using samples of urine which, according to the conventional test procedures carried out in the hospital microbiology laboratory, tested positive for *Chlamydia trachomatis*. Thus, the method of testing according to the invention identified 23 of the 24 *Chlamydia* positives. The urine samples of these 23 patients produced light response curves having common features, which features were not shown by other samples that produced a light response in the test of the invention. Although the test of the invention identified 23 of the 24 *Chlamydia* positives, it did not identify one of the 24 *Chlamydia* positives. The one *Chlamydia* positive patient not identified by the test of the invention was a man who had attended the clinic because his partner was diagnosed with *Chlamydia* although he had no symptoms and no urethral smear was taken. This patient was, nonetheless, treated in view of the *Chlamydia* positive result obtained by the clinical laboratory test.

Figure 6:
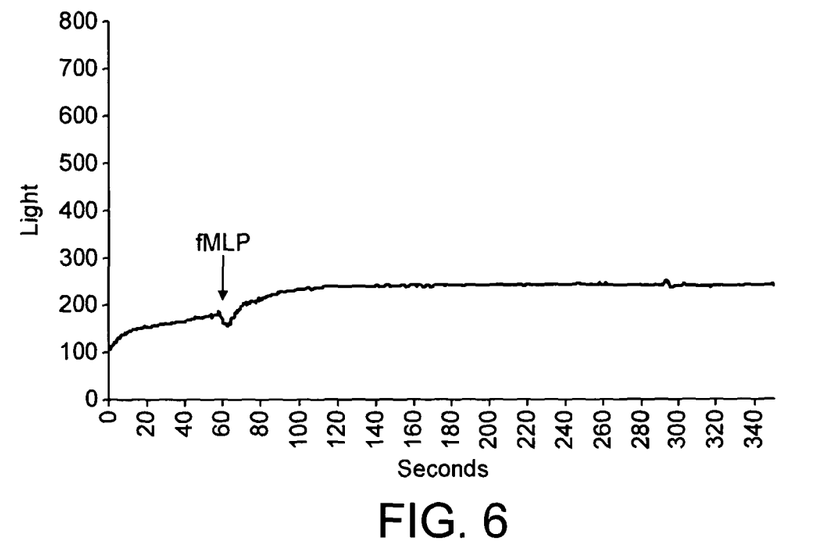
FIG. 6 provides a light response curve produced using a sample of urine taken from a male patient diagnosed with NSU.

The light response curves obtained using the urine samples of the patients also identified all 17 patients that, according to conventional clinical testing, were diagnosed as having NSU. The light response curves, although not showing the characteristic curve shape identified for the *Chlamydia* positives, did show increased light response following the addition of the activator to the sample. There did not, however, appear to be one typical shape that was common to the light response curves obtained for patients given an NSU diagnosis. This, most likely, is due to the fact that various causative infection agents may be implicated in NSU. A light response curve produced using a sample of urine taken from a male patient diagnosed with NSU is shown, by way of example, in FIG. 6. The NSU diagnosis of this patient was confirmed by light microscopical identification of Gram-stained urethral smear and the patient showed typical symptoms of the infection.

EXAMPLE 2

These experiments were carried out to evaluate the test according to the invention on samples of urine collected at a GUM (Genito Urinary Medicine) clinic at a hospital in the UK. Urine samples of 365 male patients were included in the tests.

All the male patients who came to the clinic because their partners had an infection were treated at the clinic irrespective of whether they had symptoms. Samples of urine from each patient were sent to the microbiology department for identification of *Chlamydia trachomatis* using a commercial nucleic acid amplification test (NAAT) or culture for *Neisseria gonorrhoeae* as well as being used in cell activation assays according to the invention. For all men attending the GUM clinic, a clinical decision was made as to whether to treat at the time of the visit as well as to take a urethral smear. The decision for the latter was based on whether there were symptoms, or the men had many different partners and were high risk. The diagnosis of non-specific urethritis, in which no pathogen was identified, led to treatment with antibiotics, just as it did for a positive diagnosis of *Chlamydia trachomatis*.

Figure 7:
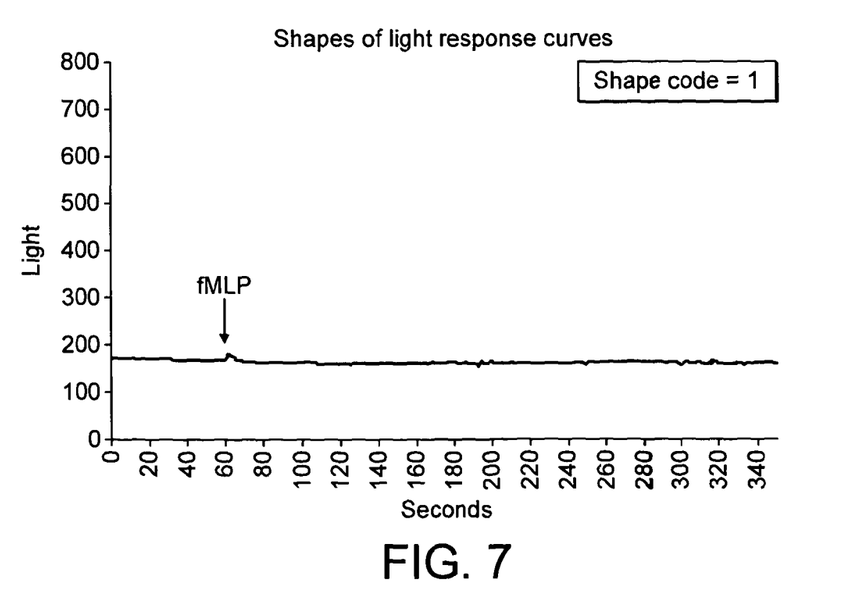
FIG. 7 provides a library of response curves.

A sample of first pass urine obtained from each male patient was subjected to testing according to the invention. The procedures used to collect the urine, to isolate the leucocytes from the urine sample and to prepare the leucocyte sample for analysis were as described above in Example 1. Light response curves were produced using the samples in accordance with the method described in Example 1 and each curve was scored according to which member of a library of curve shapes it most resembled. The library, containing five curve shapes, was assembled from curve shapes obtained by the Applicant in the course of the urine testing procedures carried out. The five curve shapes forming the library are shown in FIG. 7. The key code for the shapes was:—

Key for Shape Score

1. No response.
2. Response with decrease after initial peak.
3. Response with increase after initial peak.
4. Response with plateau after initial peak.
5. Response—with decrease after initial peak followed by increase to a second peak.

The light response of the urine samples, according to the invention, are compared in the following tables.

TABLE 1

| | | | | | | | |
|---|---|---|---|---|---|---|---|
| *Chlamydia* positive | | | | | | | |
| Patients identified as | | Method according to invention | | | | | |
| *Chlamydia* positive by clinical test | | Response curve shape score | | | | | No. | % of clinical |
| Patent type* | Number | 1 | 2 | 3 | 4 | 5 | confirmed diagnoses |
| Type 1 | 20 | 0 | 18 | 0 | 2 | 0 | 20 | 100 |
| Type 2 | 5 | 0 | 4 | 0 | 1 | 0 | 5 | 100 |
| Type 3 | 8 | 0 | 6 | 0 | 2 | 0 | 8 | 100 |
| Type 4 | 20 | 6 | 7 | 0 | 1 | 0 | 14 | 70 |

*definitions of patient types in Table 1

Type 1 - patient shows symptoms and presence of cells identified on urethral smear.

Type 2 - patient shows symptoms and either a urethral smear was not taken or a urethral smear was taken but nothing abnormal was detected.

Type 3 - patient shows no symptoms but presence of cells was identified on urethral smear.

Type 4 - patient shows no symptoms and either a urethral smear was not taken or a urethral smear was taken but nothing abnormal was detected.

Summary of Results

*Chlamydia* positive (as per clinical diagnosis) male patients represented 15% of the total (53 out of 365). The results obtained according to the invention match clinic results very closely for *Chlamydia* positive patients.

The test according to the invention identified 100% of those patients that presented with symptoms and had cells identified from microscopical examination of a urethral smear (33 out of 33).

The test according to the invention identified 100% of those patients that presented with symptoms but either had no smear taken or nothing abnormal was detected (NAD) on the smear (5 out of 5).

The test according to the invention identified 100% of those patients that presented with no symptoms but had cells identified from microscopical examination of a urethral smear (8 out of 8).

The test according to the invention identified 70% of those patients that presented with no symptoms and who either had no smear taken or nothing abnormal was detected (NAD) on the smear (14 out of 20). Of the 6 patients that were assigned a negative diagnosis by the test of the invention but subsequently were diagnosed positive by the NAAT, 3 of the 6 had come to the clinic because their partner had been diagnosed with *Chlamydia*. It was assumed that the men might have acquired *Chlamydia* bacteria from their partners but had not yet developed an inflammation. The other 3 men also did not have an inflammation and the laboratory may have identified non-viable *Chlamydia*, since NAATs do not distinguish between viable bacteria and dead or even fragments of the cell wall which are still antigenic. Also, the NAATs test does produce approximately 10% false positives and it is possible that our negative diagnosis could have been correct.

The urine sample of one patient produced an intense luminescent response, according to the method of the invention, indicative of a severe urethritis. The shape of the light emission curve corresponded with that shown in FIG. 2. Confirmation that the patient was infected with *Neisseria gonorrhoeae* was provided by gram positive staining of cells from an urethral smear and microscopical examination of living cells from the urine sample.

NSU Diagnosed by the Clinic

Patients given an NSU diagnosis from the clinic represented 10% of the total patients tested (36 out of 365).

Cell activation results obtained by the method of the invention showed positive responses for 61% of patients who were given an NSU diagnosis by the clinic (22 out of 36).

Figure 8:
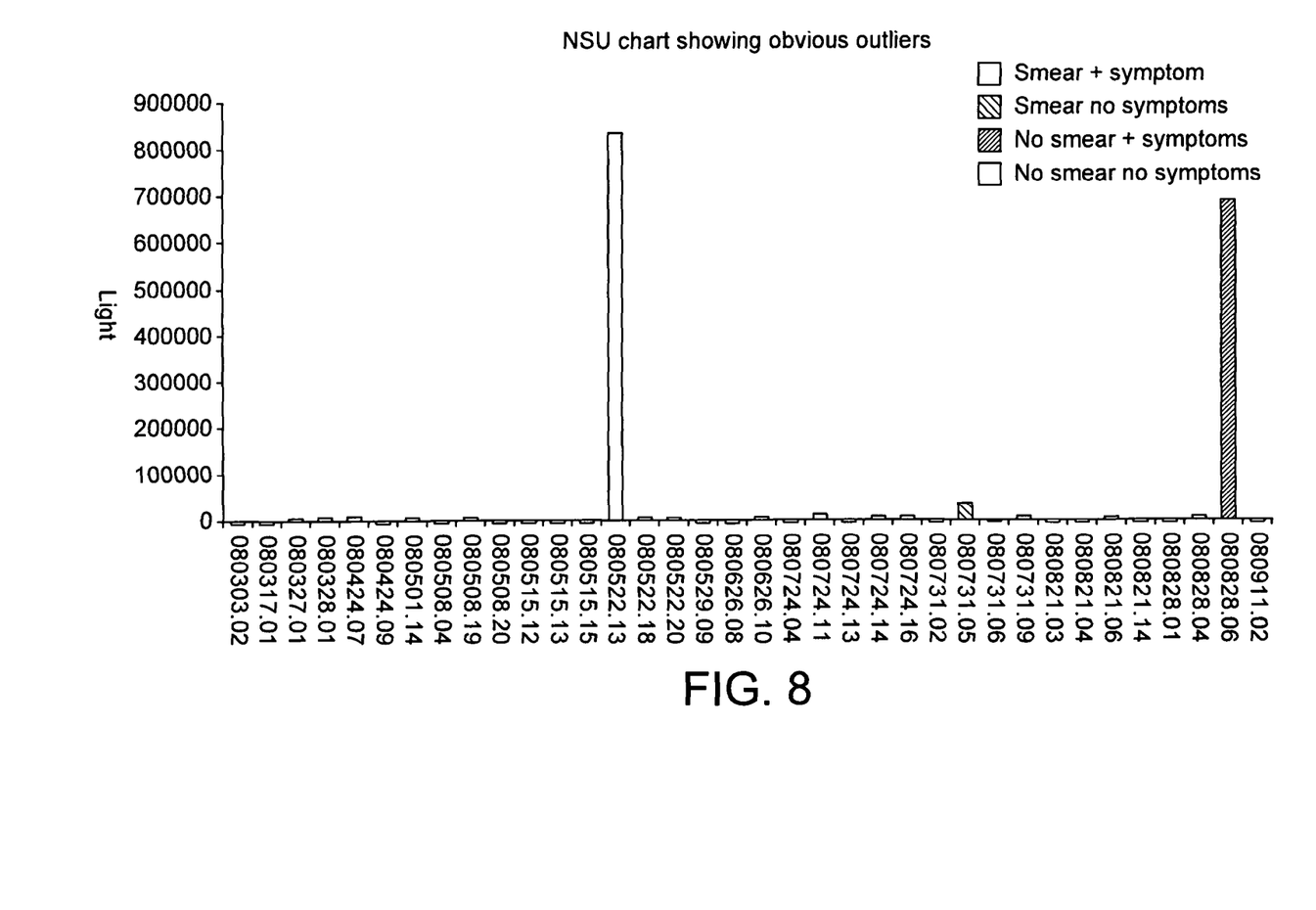
FIG. 8 provides an NSU chart showing the normalized light values and the obvious outliers.

The normalised maximum light values (total volume of urine collected adjusted so that results could be compared from patient to patient) varied between 33 and 834,080 relative light units (RLU) giving a mean of 44,763 RLU. The NSU chart showing the normalised light values and the obvious outliers is shown in FIG. 8. When the two outliers with maximum signals of 692,000 and 834,000 RLU were removed the mean NSU light signal was 2,500 RLU. Outlier with a score of 834,000 RLU was later diagnosed as a urinary tract infection. This diagnosis had been suggested as the total volume of urine collected from this patient was 99 mL which (in view of the volume) would have been a combination of first pass and midstream urine. The second outlier with a score of 692,000 RLU was not a UTI and the volume of urine collected was 23 mL. The shape of the curve of outlier 2 had some features associated with a *Chlamydia* curve but was not identified C positive by the hospital laboratory but was treated at the clinic with antibiotics.

There did not appear to be a typical shape for NSU patient cell activation responses.

Clinic Negatives

Patients given a negative diagnosis by the clinic represented 74% of the total patients tested (265 out of 365). For patients given a negative diagnosis by the clinic, the cell activation results obtained according to the invention showed positive responses for 23% (60 out of 265) of these patients, indicating a possible greater sensitivity of the assay.

The normalised maximum light values after stimulation with fMLP for clinic negative patients varied between 18 and 65,433 relative light units (RLU), with a mean of 1231 RLU, which is significantly lower than the mean maximum value for *Chlamydia* positive and NSU diagnosed patients. This is due to the fact that the majority of the clinic negative patients had maximum light values <2000 RLU (246 out of 265=93%).

For 77% of the positive results obtained by the invention for clinic negatives (46 out of 60), response curves appeared to show a plateau after the initial peak following stimulation with fMLP (shape code 4) although it is difficult to identify the shape in some instances as many of the positive results obtained by the invention for clinic negatives (50 out of 60=83%) had low maximum light values after stimulation with fMLP (<2000 RLU).

Normalised maximum light values after stimulation with fMLP for *Chlamydia* positive patients, patients given an NSU diagnosis and patients given a negative diagnosis by the clinic. Mean relative light units with and without outliers removed and median.

| | Total Number | Range | Mean RLU with outliers | Mean RLU outliers removed | Median |
|---|---|---|---|---|---|
| *Chlamydia* positive | 53 | 167-297,300 | 28,290 | — | 4880 |
| NSU | 36 | 33-834,000 | 44,760 | 2500 | 730 |
| Clinic negatives | 265 | 18-65,400 | 1,120 | 753 | 390 |

Further Investigations

A number of urine samples that produced positive light response curves according to the present invention were also sent away for bespoke polymerase chain reaction (PCR) amplification tests for *Chlamydia trachomatis, Mycoplasma genitalium, Mycoplasma hominis, Ureaplasma urealyticum* and *Trichomonas vaginalis*. In 100% of cases (five in number) positive diagnosis of *Chlamydia trachomatis*, confirmed in the hospital automated PCR as well as the bespoke PCR, was matched by positive light response curves according to the present invention. There were, in addition, five instances in which patients had been sent away from the clinic with negative diagnoses although the urine samples provided by these patients had produced positive light response curves according to the present invention. Even though these five patients had nothing abnormal detected from a urethral smear, three of them had presented with symptoms. The urine samples of these five patients were submitted, as stated above, to the bespoke PCR tests. These tests identified one of the five patients as being infected by both *Mycoplasma hominis* and *Ureaplasma urealyticum*, two other patients as having *Ureaplasma urealyticum* infections and another patient as having *Mycoplasma hominis* infection. A patient who had provided a urine sample which produced a positive light response curve according to the present invention had been diagnosed by the clinic with a non-specific urethritis (NSU) after cells were identified on a urethral smear was subsequently identified, from the bespoke PCT test, to be infected with *Mycoplasma genitalium*. Finally, a patient whose urine sample produced a positive light response curve according to the present invention was found, by a subsequent blood test, to be infected with syphilis.

It is clear, from the above, that the present invention provides a simple yet very sensitive method of detecting inflammation in the urinary tract or urethra of a patient.

Magnitude of Light Response as an Indication of Degree of Inflammation

The normalised maximum light values after stimulation with fMLP for *Chlamydia* positive patients varied between 167 and 297,290 relative light units (RLU) with a mean of 28,291 RLU.

The typical shape for *Chlamydia* positive patients appears to be that of shape code 2 in FIG. 7 (initial peak after stimulation with fMLP followed by a significant decrease in light). Of *Chlamydia* positive results that were also positive according to the method of the invention, 83% had this shape (39 out of 47).

Quantifying the inflammatory response could be valuable in selecting those individuals who should be invited back for an appointment to establish a test of cure. Also, it might be that some individuals diagnosed with NSU might have a residual inflammation from a previous infection that was treated with antibiotics or disappeared on its own. These follow-up appointments could prove valuable in understanding more about NSU as well as determining the potential role quantifying inflammation has in controlling the spread of STIs in the community.

The invention claimed is:

1. A method for detecting inflammation in the urinary tract or urethra of a patient, which method comprises
    a) contacting leucocytes obtained from a urine sample provided by the patient with a luminescence reagent which emits light on reaction with an oxidant;
    b) adding an activator to the mixture of leucocytes and luminescence reagent;
    c) continuously monitoring and/or measuring light emitted by the luminescence reagent over a predetermined time period commencing before and ending after the addition of the activator to obtain a light emission curve and comparing the obtained light emission curve to a standard light emission curve to detect the presence or absence of inflammation in the urinary tract or urethra of the patient.

2. A method according to claim 1 for detecting urethritis in a patient comprising
    a) contacting urethral leucocytes obtained from a urine sample provided by the patient with a luminescence reagent which emits light on reaction with an oxidant;
    b) adding an activator to the mixture of leucocytes and luminescence reagent; and
    c) continuously monitoring and/or measuring light emitted by the luminescence reagent over a predetermined time period commencing before and ending after the addition of the activator to obtain the light emission curve.

3. A method according to claim 2, wherein the urine sample is a sample of first pass urine.

4. A method according to any one of claims 1 to 3, wherein the luminescence reagent is the photoprotein derived from *Pholas dactylus*.

5. A method according to claim 1, wherein the activator is selected from N-formyl-methionyl-leucyl-phenylalanine, platelet activating factor, Phorbol-12-myristate-13-acetate and lipopolysaccharide.

6. A method according to claim 2, the method comprises comparing the obtained light emission curve with a library of standard signature curves obtained for bacterial sexually transmitted infections.

7. A method according to either claim 2, wherein the patient is a human male patient.

8. A method of diagnosing an urethral infection selected from *Chlamydia trachomatis* and *Neisseria gonorrhoeae* in a patient comprising
    a) contacting urethral leucocytes obtained from a sample of first pass urine provided by the patient with a luminescence reagent which emits light on reaction with an oxidant;
    b) adding an activator to the mixture of leucocytes and luminescence reagent;
    c) continuously measuring light emitted by the luminescence reagent over a predetermined time period commencing before and ending after the addition of the activator and producing therefrom a light emission curve;
    d) comparing the light emission curve with standard signature light emission curves obtained for leucocytes known to be infected by *Chlamydia trachomatis* or by *Neisseria gonorrhoeae*;
    e) diagnosing the presence or absence of infection from the result of the comparison in step d).

9. A method according to claim 8, wherein the patient is a human male patient.

10. A method according to either claim 8 or claim 9, wherein the luminescence reagent is the photoprotein derived from *Pholas dactylus*.

11. A method according to claim 8, wherein the activator is selected from N-formyl-methionyl-leucyl-phenylalanine, platelet activating factor and Phorbol-12-myristate-13-acetate.

12. A method of diagnosing non-specific urethritis in a patient comprising:
    a) contacting urethral leucocytes obtained from a sample of first pass urine provided by the patient with a luminescence reagent which emits light on reaction with an oxidant;
    b) adding an activator to the mixture of leucocytes and luminescence reagent;
    c) continuously measuring light emitted by the luminescence reagent over a predetermined time period commencing before and ending after the addition of the activator and producing therefrom a light emission curve;
    d) comparing the light emission curve obtained with a control curve and with standard signature light emission curves obtained for leucocytes known to be infected by *Chlamydia trachomatis* or by *Neisseria gonorrhoeae*;
    e) diagnosing the presence or absence of a non-specific urethritis infection on the basis of the results of the comparison in step d).

* * * * *